(12) United States Patent
Rishton et al.

(10) Patent No.: US 7,723,377 B2
(45) Date of Patent: May 25, 2010

(54) INHIBITORS OF COGNITIVE DECLINE

(75) Inventors: Gilbert M Rishton, Malibu, CA (US); Hiromi Arai, Simi Valley, CA (US); Zoya Kai, La Jolla, CA (US); Cody Lee Fullenwider, Ojai, CA (US); Kristin Beierle, Thousand Oaks, CA (US)

(73) Assignee: Cognition Therapeutics, Inc., Pittsburgh, PA (US)

( * ) Notice: Subject to any disclaimer, the term of this patent is extended or adjusted under 35 U.S.C. 154(b) by 145 days.

(21) Appl. No.: 11/863,549

(22) Filed: Sep. 28, 2007

(65) Prior Publication Data
US 2008/0193574 A1    Aug. 14, 2008

Related U.S. Application Data

(60) Provisional application No. 60/827,630, filed on Sep. 29, 2006.

(51) Int. Cl.
*A61K 31/40* (2006.01)
*C07D 295/00* (2006.01)

(52) U.S. Cl. ..................................... 514/428; 548/570
(58) Field of Classification Search ................. 548/570; 514/428
See application file for complete search history.

(56) References Cited

U.S. PATENT DOCUMENTS 6,518,315 B1    2/2003    Roufogalis et al.

FOREIGN PATENT DOCUMENTS

| DE | 10320560 | 1/2004 |
| JP | 2003-113117 | 4/2003 |
| WO | WO 0130335 | 5/2001 |
| WO | WO 2006138349 | 12/2006 |

OTHER PUBLICATIONS

Aboul-Enein et al., 2006, CAS: 147:10056.*
Negron et al., 1992, CAS: 117: 26230.*
Citron, M. et al., "Evidence that the 42- and 40-amino acid forms of amyloid beta protein are generated from the beta-amyloid precursor protein by different protease activities," Proc. Natl. Acad. Sci. USA, Nov. 1996, pp. 13170-13175, vol. 93.
Denniff, P., "Syntheses of the (±)-[n]-Gingerols (Pungent Principles of Ginger) and Related Compounds through Regioselective Aldol Condensations: Relative Pungency Assays," J. Chem. Soc. Perkin I (1981) pp. 82-87.
Fukumoto, H. et al., "Beta-Secretase Activity Increases with Aging in Human, Monkey, and Mouse Brain," American Journal of Pathology, Feb. 2004, pp. 719-725, vol. 164, No. 2.
Grzanna, R. et al, "Ginger Extract Inhibits Beta-Amyloid Peptide-Induced Cytokine and Chemokine Expression in Cultured THP-1 Monocytes," The Journal of Alternative and Complementary Medicine, 2004, pp. 1009-1013, vol, 10, No. 6.
Mustafa, T. et al., "Drug Development Report (9): Pharmacology of Ginger, Zingiber Officinale," J. Drug Dev. 1993, vol. 6(1):25-39.
Masuda, Y. et al., "Antioxidant properties of gingerol related compounds from ginger," BioFactors, 2004, pp. 293-296, vol. 21.
Rishton, G.M. et al., "Computational approaches to the prediction of blood-brain barrier permeability: A comparative analysis of central nervous system drugs versus secretase inhibitors for Alzheimer's disease," Current Opinion in Drug Discovery & Development, 2006, pp. 303-313, vol. 9, No. 3.
Shin, S.-G. et al., "Zingerone as an Antioxidant against Peroxynitrite," Journal of Agricultural and Food Chemistry, 2005, pp. 7617-7622, vol. 53.
Surh, Y.-J. et al., "Enzymic Reduction of [6]-Gingerol, a Major Pungent Principle of Ginger, in the Cell-Free Preparation of Rat Liver," Life Sciences, (1994), vol. 54(19)321-326.
Kimura, Chemical Structural Requirement in Gingerol Derivatives for Potentiation of Prostaglandin F2alpha-Induced Contraction in Isolated Mesenteric Veins of Mice, 1989, J. Pharmacobio-Dyn. 12:220-227.

* cited by examiner

*Primary Examiner*—Rei-tsang Shiao
(74) *Attorney, Agent, or Firm*—Pepper Hamilton LLP

(57) ABSTRACT

Compounds that are central nervous system drug candidates for the treatment of cognitive decline and, more particularly, Alzheimer's disease are provided. Methods of treating, inhibiting, and/or abatement of cognitive decline and Alzheimer's disease with a derivative of ginger oil are also provided. Also provided is a method of conditioning biological extracts, such as a medicinal plant extract, by a reductive amination process to give nitrogen-containing derivatives.

6 Claims, 3 Drawing Sheets

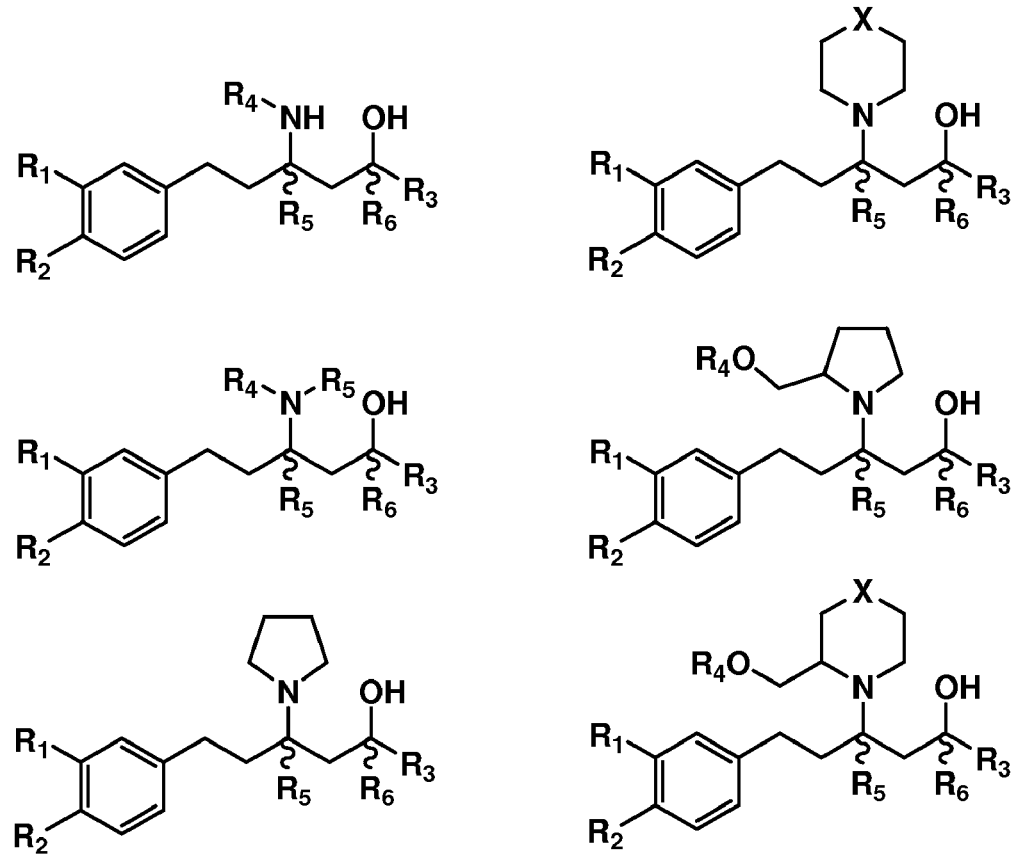

R₁ = H, -OH, -OCH₃, -F, -Cl, -CF₃, small alkyl, small alkoxy, etc.

R₂ = H, -OH, -OCH₃, -F, -Cl, -CF₃, small alkyl, small alkoxy, etc.

R₃ = H, -CH₃, -CH₂CH₃, -CH₂(CH₂)$_{1-7}$CH₃, branched alkyl, cycloalkyl, cycloaryl, cyclic heteroaryl, etc.

R₄ = H, CH₃, small alkyl, cycloalkyl, cycloaryl, etc.

R₅ = H, CH₃, small alkyl, cycloalkyl, cycloaryl, etc.

R₆ = H, CH₃, small alkyl, cycloalkyl, cycloaryl, etc.

X = CH₂, N, O, S, N-R, where R = H, CH₃, small alkyl, cycloalkyl, cycloaryl, etc.

FIGURE 1

INHIBITORS OF COGNITIVE DECLINE

CROSS-REFERENCE TO RELATED APPLICATION

The present application claims priority of U.S. Provisional Patent Application 60/827,630 titled "Unnatural Beta-Secretase Inhibitors Derived From Conditioned Extraction of Ginger Root," filed Sep. 29, 2006, the entire contents of which is hereby incorporated herein by reference.

BACKGROUND

Cognitive decline, such as memory loss, confusion, impaired judgment, personality changes, disorientation, and loss of language skills occurs in much of the population as they age, in varying degree. The most common, severe and irreversible form of cognitive decline is Alzheimer's disease, which, at present, is always fatal.

The symptoms of cognitive decline and Alzheimer's disease are thought to stem from the formation of amyloid plaques and neurofibrillary tangles, which are thought to contribute to the degradation of the neurons (nerve cells) in the brain and the subsequent onset of symptoms. Amyloid is a general term for protein fragments that the body produces normally. Beta-amyloid is a fragment of a protein that is snipped from another protein called amyloid precursor protein (APP). In a healthy brain, beta-amyloid protein fragments are broken down and eliminated. In individuals with Alzheimer's disease and other forms of cognitive decline, the fragments accumulate to form hard, insoluble plaques. Neurofibrillary tangles are insoluble twisted fibers that are found inside of the brain's cells. The protein contained in neurofibrillary tangles, i.e., the tau protein, forms a microtubule, which helps transport nutrients and other important substances from one part of the nerve cell to another. In Alzheimer's disease the tau protein is abnormal and the microtubule structures collapse.

Beta-secretase is the enzyme in the human brain responsible for the production of Beta-amyloid, the pathogenic substance responsible for the formation of brain plaques and tangles in the Alzheimer's diseased brain. See, e.g., Citron et al., Proc. Natl. Acad. Sci., USA (1996) 93(23): 13170-13175. Beta-amyloid and its oligomers are also believed to be responsible for early cognitive decline in the pre-Alzheimer's diseased brain. Inhibition of beta-secretase would be expected to lessen beta-amyloid burden in the brain and thus slow cognitive decline, block the formation of amyloid oligomers, the production of plaques and tangles, halt neurodegeneration, and to potentially treat mild cognitive impairment and more serious forms of cognitive impairment such as Alzheimer's disease.

The gingerols are a series of natural small molecules isolated from ginger, *Zingiber Officinale*, and are classified according to their alkyl chain length e.g., [6]-gingerol, [8]-gingerol. Gingerols are known to be relatively unstable under both chemical and biological conditions, forming inactive substances. For example, the beta-hydroxycarbonyl function of the gingerols is vulnerable to oxidation or dehydration to form inactive products, and the gingerols are particularly prone to rapid dehydration under acidic conditions, such that even the pure substance is difficult to store for long periods. Further information on gingerols can be found in, for example, Deniff et al., *J. Chem. Soc. Perkin I*, 1981, 82-87; Mustafa, et al., *J. Drug Dev.*, 1993, 6, 25-39; and Young-Joon et al., *Life Sciences*, 1994, 54, PL 321-326. Accordingly, simple oral dosing of the gingerols for medicinal action might not be possible due to the acidic environment of the stomach and upper intestinal tract. Further, chemical and biological instability is also likely to be a serious problem for intravenous doses. Accordingly, there is strong need to discover inhibitors of cognitive decline, and in particular, compounds that are useful in the treatment and abatement of cognitive decline and Alzheimer's disease, by methods such as inhibiting amyloid production, aggregation, and/or deposition (i.e., plaqing), inhibiting neuorodegeneration, and/or restoring long term potentiation. There is also a need for inhibitors of cognitive decline that are chemically and biologically stable.

Plants have attracted relatively little attention as potentially valuable resources for drug discovery in the area of cognitive decline and Alzheimer's disease. The use of plant extracts to produce unnatural derivatives of compounds of medicinal interest is not generally used. Accordingly, there is also a need for a method of producing compounds of medicinal interest from plant extracts and extracts from other biological sources. In particular, there is also a need to produce and identify compounds derived from plant extracts that are useful in the treatment and abatement of cognitive decline and Alzheimer's disease.

SUMMARY

The present invention satisfies the above identified needs. According to the present invention, compounds useful for inhibiting, treating, or abatement of cognitive decline are provided. In a method called "chemical conditioning", the compounds of the present invention are derived from naturally occurring compounds, such as those found in medicinal plants, like ginger. The chemical conditioning process described herein is applicable to a large variety of biological extracts and may be used to create compound arrays for screening for potential new drug candidates. Further, in general, compounds derived by the chemical conditioning process are chemically stable and structurally diverse, and good candidates for use in drug screenings for pharmaceutical activity.

According to one embodiment of the invention, compounds derived from ginger oil are provided. The compounds show activity in a beta-secretase assay and are potentially useful for the inhibition, treatment, and abatement of cognitive decline and Alzheimer's disease. Preferably, the derivatives of ginger oil are nitrogen containing, and more preferably, the derivative of ginger oil is compound in purified and isolated form. The compounds and methods described herein may be used to treat one or more symptoms of cognitive decline and/or Alzheimer's disease such as memory loss, confusion, impaired judgment, personality changes, disorientation, and loss of language skills. Further, the compounds and methods described herein may be useful in inhibiting, treating, and/or abating cognitive decline and/or Alzheimer's disease by restoring long term potentiation, and/or inhibiting, treating, or abatement of one or both of neurodegeneration and general amyloidosis, more specifically, by inhibiting, treating, or abatement of one or more of amyloid production, amyloid assembly, amyloid aggregation, amyloid oligomer binding, and amyloid deposition.

According to another embodiment of the invention, compounds derived from ginger oil by the chemical conditioning process described herein are provided. Preferably, compounds according to the present invention are compounds of Formulas I, II, and III:

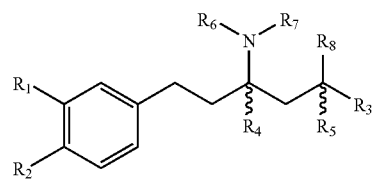

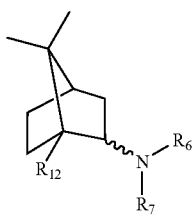

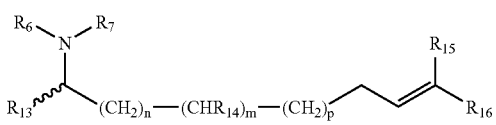

and pharmaceutically acceptable salts and prodrugs thereof, wherein, $R_1$ and $R_2$ are each independently selected from the group consisting of hydrogen, hydroxy, methoxy, halide, haloalkyl, small alkyl, and small alkoxy;

$R_3$, $R_4$ and $R_5$ are each independently selected from the group consisting of hydrogen, small alkyl, cycloalkyl, heterocyclyl, heterocyclylalkyl, aryl, arylalkyl, heteroaryl, and heteroarylalkyl;

$R_6$ and $R_7$ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or $R_6$ and $R_7$ along with the nitrogen to which they are attached form a five or six membered heterocyclic ring, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —$CH_2OR_9$;

$R_8$ is selected from the group consisting of hydroxy, small alkoxy, and —$NR_{10}R_{11}$;

$R_9$ is selected from the group consisting of hydrogen, small alkyl, cycloalkyl, heterocyclyl, heterocyclylalkyl, aryl, arylalkyl, heteroaryl, and heteroarylalkyl;

$R_{10}$ and $R_{11}$ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or $R_{10}$ and $R_{11}$ along with the nitrogen to which they are attached form a five or six membered heterocyclic ring, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —$CH_2OR_9$;

$R_{12}$ is selected from the group consisting of hydrogen, haloalkyl, and small alkyl;

$R_{13}$ is selected from the group consisting of hydrogen, and small alkyl;

$R_{14}$ is selected from the group consisting of hydrogen, and small alkyl;

$R_{15}$ and $R_{16}$ are each independently selected from the group consisting of hydrogen, small alkyl, cycloalkyl, heterocyclyl, heterocyclylalkyl, aryl, arylalkyl, heteroaryl, and heteroarylalkyl; and n, m, and p are each independently 0, 1, or 2.

Preferably, compounds according to Formula I include the compounds of the formula:

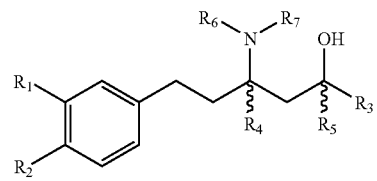

and pharmaceutically acceptable salts and prodrugs thereof, wherein, $R_6$ and $R_7$ along with the nitrogen to which they are attached form a five or six membered heterocyclic ring of the formula:

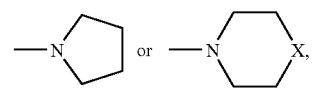

wherein,

X is selected from the group consisting of —$CH_2$, —$CHR_{17}$, —$N=$, —$O$—, —$S$—, and —$N$—$R_{17}$, wherein each carbon atom of the five or six membered heterocyclic ring, individually, is unsubstituted, or substituted with a substituent selected from the group consisting of hydroxy, hydroxyalkyl, halide, haloalkyl, small alkyl, small alkoxy, and —$CH_2OR_9$; and $R_{17}$ is selected from the group consisting of hydrogen, small alkyl, hydroxyalkyl, cycloalkyl, heterocyclyl, heterocyclylalkyl, aryl, arylalkyl, heteroaryl, and heteroarylalkyl.

More preferably, compounds according to Formula I include compounds of the formula:

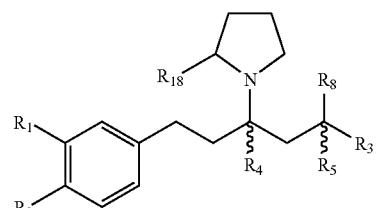

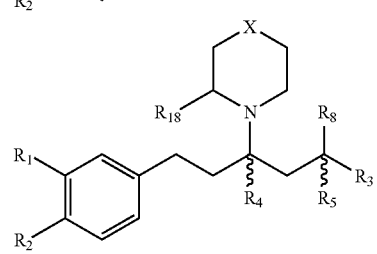

-continued

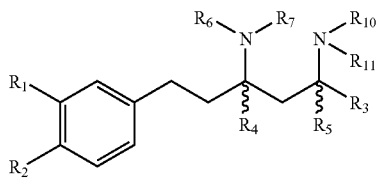

and pharmaceutically acceptable salts and prodrugs thereof, wherein, $R_{18}$ is selected from the group consisting of hydrogen, hydroxy, hydroxyalkyl, halide, haloalkyl, small alkyl, small alkoxy, and —$CH_2OR_9$.

Preferred compounds according to Formula III include compounds of the formula:

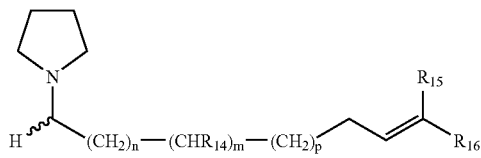

and pharmaceutically acceptable salts and prodrugs thereof, wherein, $R_{14}$, $R_{15}$ and $R_{16}$ are each independently small alkyl;

n and m are each independently 0 or 1; and p is 1 or 2.

Most preferably, compounds according to Formulas I, II, and II include the compounds shown in FIG. 3, and pharmaceutically acceptable salts and prodrugs thereof. Also most preferably, compounds according to the present invention exhibit activity in a beta-secretase assay.

In another embodiment, the invention comprises a compound according to Formula I, II, and/or III in a pharmaceutically-acceptable carrier.

In another embodiment, the invention comprises a method of inhibiting, treating, or abatement of cognitive decline and/or Alzheimer's disease comprising the administration of a compound according to Formula I, II, and/or III to a patient.

In another embodiment, the invention comprises a method of preparing an array of chemical compounds from a biological extract. According to the method, a biological extract is provided. The biological extract has one or more biological compounds, and each biological compound has one or more reactive electrophilic groups. Preferably, the biological extract is a plant extract, and/or the reactive electrophilic group is an aldehyde or a ketone. Then, the biological compounds in the extract are reacted with an amine to incorporate the amine into the biological compounds. The biological compounds having the incorporated amine are then reacted with a reducing agent to form an array of one or more chemical compounds. The one or more chemical compounds are derivatives of the biological compounds in the biological extract. Preferably, the biological compounds are nitrogen-containing. The chemical compounds may then be isolated and/or purified, and screened for biological activity. More preferably, the chemical compounds are derived from a plant extract and are screened for biological activity.

FIGURES

These and other features, aspects and advantages of the present invention will become better understood from the following description, appended claims, and accompanying figures where:

FIG. 1 shows exemplary and isolated aromatic compounds of the invention for the treatment of cognitive impairment and Alzheimer's disease.

DETAILED DESCRIPTION

Figure 2:
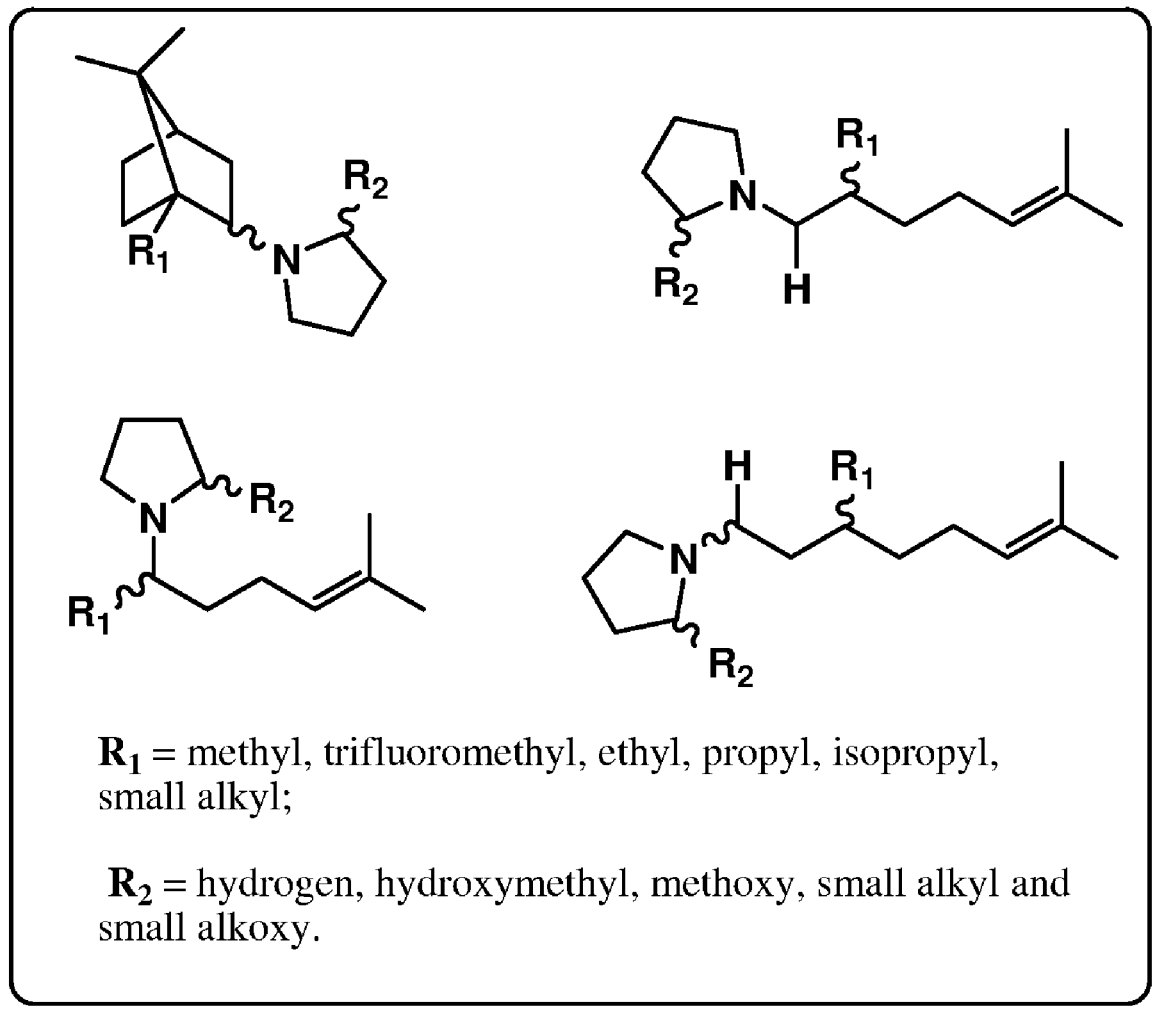
FIG. 2 shows exemplary and isolated non-aromatic compounds of the invention for the treatment of cognitive impairment and Alzheimer's disease.

The present invention provides a method of inhibiting, treating, or abatement of cognitive decline, comprising administering a nitrogen-containing derivative of ginger oil to a subject, i.e., a mammal. Also, the present invention provides compounds that are nitrogen-containing derivatives of ginger oil. The compounds of the present invention show activity in a beta-secretase assay and are potentially useful as a therapeutic agent for the treatment and prevention of Alzheimer's disease, and for the treatment of the symptoms of cognitive decline, such as memory loss, confusion, impaired judgment, personality changes, disorientation, or loss of language skills, by, for example, inhibiting, treating, or the abatement of one or more of amyloid production, amyloid aggregation, and amyloid deposition. In addition, the compounds of the present invention may be used for inhibiting, treating, or abatement of neurodegeneration and general amyloidosis, and may be used for treating, and/or the abatement of cognitive decline such as by the restoration of long term potentiation.

In another aspect, the present invention provides a two step reductive amination process for preparing a derivative of a biological extract, such as a medicinal plant extract. This method has wide-ranging applications in the field of drug discovery using common and medicinal plants. This method has been employed in the present invention for the discovery of beta-secretase inhibitors derived from the extract of ginger root.

For the purpose of this disclosure, the following terms have the following meanings.

The term "small alkoxy" as used herein refers to a small alkyl group attached to the parent molecular group through an oxygen atom. Examples of alkoxy groups include methoxy, ethoxy, isopropoxy, and t-butoxy.

The term "small alkyl" as used herein refers to a saturated straight or branched chain group of 1-8 carbon atoms derived from an alkane by the removal of one hydrogen atom. Examples of alkyl groups include methyl, ethyl, n-propyl, isopropyl and t-butyl.

The term "aryl" as used herein refers to a mono- or bicyclic carbocyclic ring system having one or two aromatic rings. The aryl group can also be fused to a cyclohexane, cyclohexene, cyclopentane or cyclopentene ring. The term "aryl" is also intended to encompass the term "phenyl", i.e., a monocyclic carbocyclic ring system having one aromatic ring.

The term "arylalkyl" as used herein refers to an aryl group attached to the parent molecular group through an alkyl group.

The term "cycloalkyl" as used herein refers to a monovalent saturated cyclic or bicyclic hydrocarbon group of 3-12 carbons derived from a cycloalkane by the removal of a single hydrogen atom.

The term "cycloalkylalkyl" as used herein refers to a cycloalkyl group attached to the parent molecular group through an alkyl group.

The terms "halo" or "halogen" as used herein refers to F, Cl, Br, or I.

The term "haloalkyl" as used herein refers to a small alkyl group substituted with one or more halogen atoms.

The terms "heterocycle" and "heterocyclyl", represent a 5-, 6- or 7-membered ring containing one, two or three heteroatoms independently selected from the group consisting of nitrogen, oxygen and sulfur. The 5-membered rings have zero to two double bonds and the 6-and 7-membered rings have zero to three double bonds. The term "heterocycle" or "heterocyclyl" as used herein additionally refers to bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Examples of heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like. Heterocyclics also include bridged bicyclic groups where a monocyclic heterocyclic group is bridged by an alkylene group.

The term "hydroxyalkyl" as used herein refers to a hydroxy radical attached to the parent molecular group through a small alkyl group.

As will be understood by those of skill in the art by reference to this disclosure, the small alkyl, small alkoxy, cycloalkyl, haloalkyl, heterocyclyl, heterocyclylalkyl, aryl, arylalkyl, heteroaryl, heteroarylalkyl, and hydroxyalkyl groups as described herein may be unsubstituted, or substituted with one or more substituents such as hydroxyl, halide, haloalkyl, small alkyl, and small alkoxy.

The term "biological compound" as used herein refers to a chemical compound that occurs in nature.

The term "biological extract" as used herein refers to an extract from a biological sample, such as a plant extract, or other extract from organic matter, containing chemical compounds that occur in nature.

The term "reactive electrophilic group" as used herein refers to an atom or group of atoms that has the ability to react with a nucleophile.

The term "nitrogen-containing derivative" as used herein represents those derivatives containing a nitrogen atom, where the nitrogen atom is a substitution another atom, such as oxygen in the parent compound.

The term "pharmaceutically-acceptable prodrugs" as used herein represents those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" as used herein represents compounds which are rapidly transformed in vivo to the parent compound of the above formula, for example, by hydrolysis in blood.

The term "pharmaceutically acceptable salt" as used herein refers to salts prepared from pharmaceutically acceptable non-toxic bases including inorganic and organic bases. Examples of suitable pharmaceutically acceptable salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

Compounds of the present invention can exist as stereoisomers wherein asymmetric or chiral centers are present. The present invention contemplates various stereoisomers and mixtures thereof. Stereoisomers include enantiomers and diastereomers, and mixtures of enantiomers or diastereomers are designated. Individual stereoisomers of compounds of the present invention can be prepared synthetically from commercially available starting materials which contain asymmetric or chiral centers or by preparation of racemic mixtures followed by resolution well-known to those of ordinary skill in the art.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring.

The term "comprise" and variations of the term, such as "comprising" and "comprises," are not intended to exclude other additives, components, integers or steps.

According to one embodiment, compounds according to Formulas I, II, and III, below are provided.

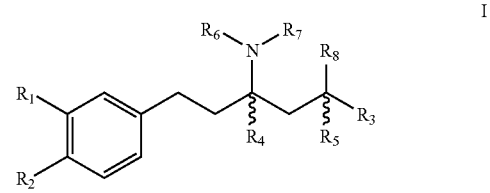

I

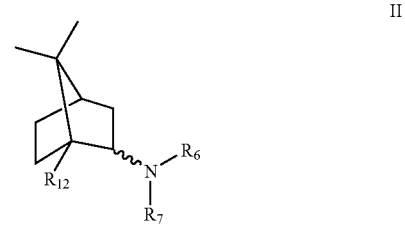

II

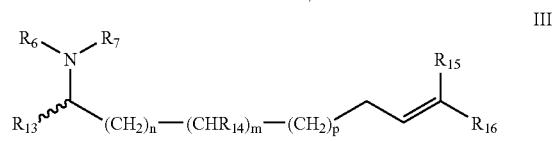

III and/or pharmaceutically acceptable salts and prodrugs thereof, wherein,

R₁ and R₂ are each independently selected from the group consisting of hydrogen, hydroxy, methoxy, halide, haloalkyl, small alkyl, and small alkoxy;

R₃, R₄ and R₅ are each independently selected from the group consisting of hydrogen, small alkyl, cycloalkyl, heterocyclyl, heterocyclylalkyl, aryl, arylalkyl, heteroaryl, and heteroarylalkyl;

R₆ and R₇ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or R₆ and R₇ along with the nitrogen to which they are attached form a five or six membered heterocyclic ring, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —CH₂OR₉;

R₈ is selected from the group consisting of hydroxy, small alkoxy, and —NR₁₀R₁₁;

R₉ is selected from the group consisting of hydrogen, small alkyl, cycloalkyl, heterocyclyl, heterocyclylalkyl, aryl, arylalkyl, heteroaryl, and heteroarylalkyl;

R₁₀ and R₁₁ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or R₁₀ and R₁₁ along with the nitrogen to which they are attached form a five or six membered heterocyclic ring, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —CH₂OR₉;

R₁₂ is selected from the group consisting of hydrogen, haloalkyl, and small alkyl;

R₁₃ is selected from the group consisting of hydrogen, and small alkyl;

R₁₄ is selected from the group consisting of hydrogen, and small alkyl;

R₁₅ and R₁₆ are each independently selected from the group consisting of hydrogen, small alkyl, cycloalkyl, heterocyclyl, heterocyclylalkyl, aryl, arylalkyl, heteroaryl, and heteroarylalkyl; and n, m, and p are each independently 0, 1, or 2.

According to one embodiment, compounds according to Formula I comprise compounds of Formula I(a):

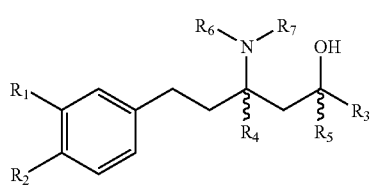

and/or a pharmaceutically acceptable salts and prodrugs thereof, wherein,

R₆ and R₇ along with the nitrogen to which they are attached form a five or six membered heterocyclic ring of the formula:

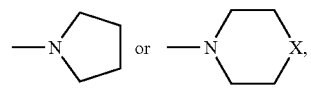

wherein,

X is selected from the group consisting of —CH₂, —CHR₁₇, —N=, —O—, —S—, and —N—R₁₇, wherein each carbon atom of the five or six membered heterocyclic ring, individually, is unsubstituted, or substituted with a substituent selected from the group consisting of hydroxy, hydroxyalkyl, halide, haloalkyl, small alkyl, small alkoxy, and —CH₂OR₉; and R₁₇ is selected from the group consisting of hydrogen, small alkyl, hydroxyalkyl, cycloalkyl, heterocyclyl, heterocyclylalkyl, aryl, arylalkyl, heteroaryl, and heteroarylalkyl.

More preferably, compounds according to Formula I comprise compounds of Formula I(a)i, I(a)ii; and I(a)iii:

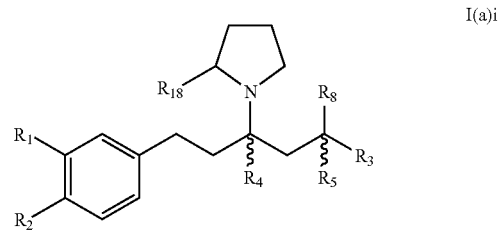

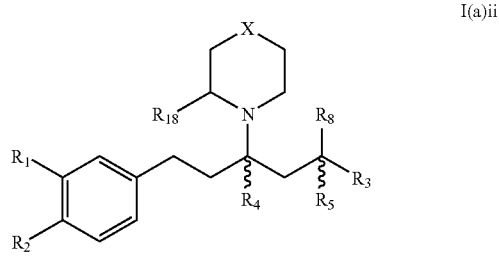

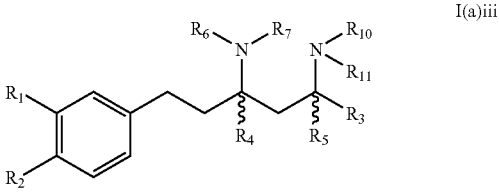

and/or a pharmaceutically acceptable salts and prodrugs thereof, wherein R₁₈ is hydrogen, hydroxy, hydroxyalkyl, halide, haloalkyl, small alkyl, small alkoxy, and —CH₂OR₉.

Most preferably, compounds according to Formula I comprise compounds of the formulas:

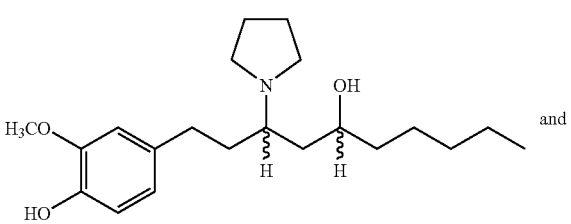

and

-continued

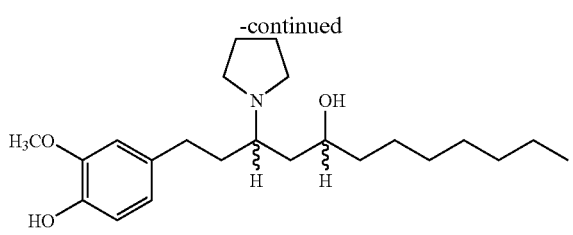

and/or pharmaceutically acceptable salts and prodrugs thereof.

According to another embodiment, compounds according to Formula II comprise compounds of Formula IIa:

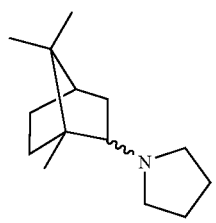

IIa and/or pharmaceutically acceptable salts and prodrugs thereof.

According to another embodiment, compounds according to Formula III comprise compounds of Formula III(a):

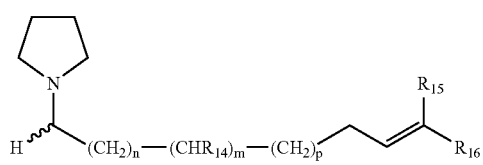

IIIa and/or pharmaceutically acceptable salts and prodrugs thereof, wherein, $R_{14}$, $R_{15}$ and $R_{16}$ are each independently small alkyl;

n and m are each independently 0 or 1; and p is 1 or 2.

More preferably, compounds according to Formula III comprise compounds of Formulas III(a)i; III (a) ii; and III (a) iii:

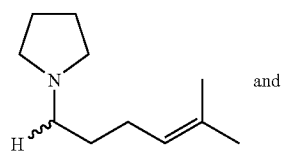

III(a)i and

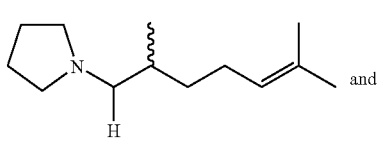

III(a)ii and

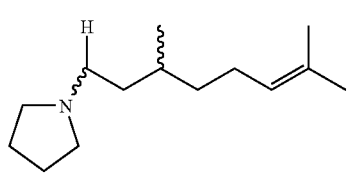

III(a)iii and/or pharmaceutically acceptable salts and prodrugs thereof.

According to another preferred embodiment, compounds according to Formulas I, II, and III, as shown by compound numbers 1-18 below are provided.

| Compound Number | Structure |
|---|---|
| 1 | 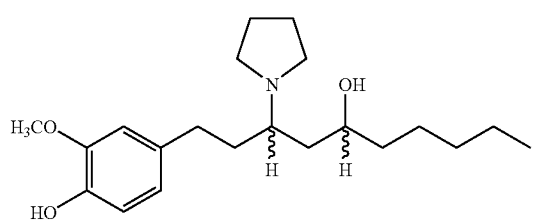 |
| 2 | 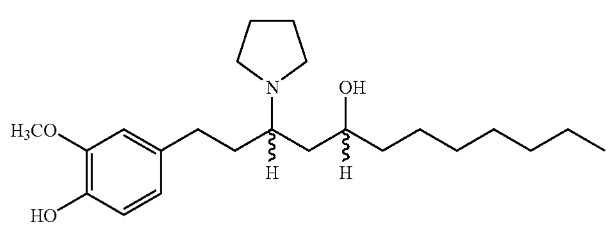 |

-continued
| Compound Number | Structure |
|---|---|
| 3 | 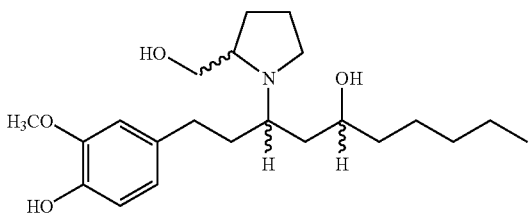 |
| 4 | 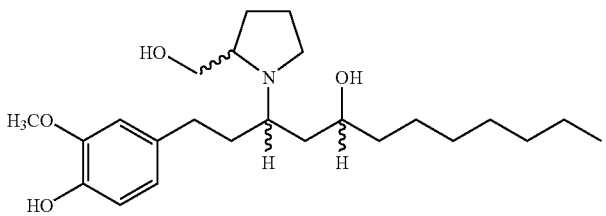 |
| 5 | 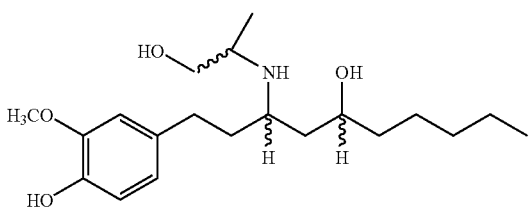 |
| 6 | 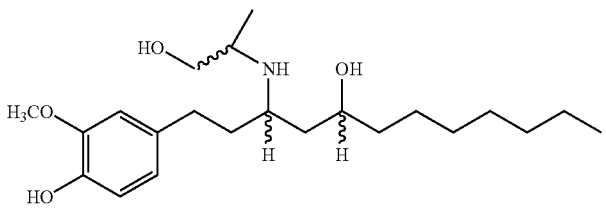 |
| 7 | 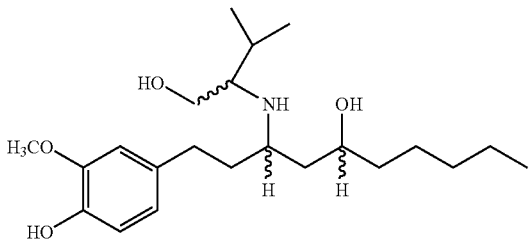 |
| 8 | 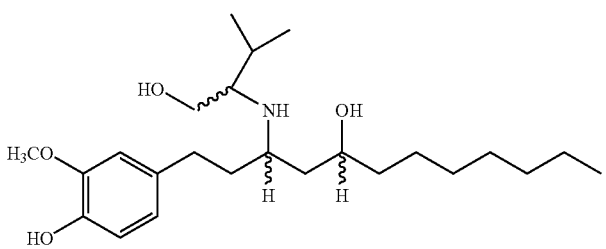 |

-continued
| Compound Number | Structure |
|---|---|
| 9 | 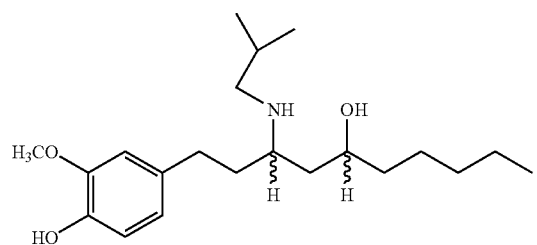 |
| 10 | 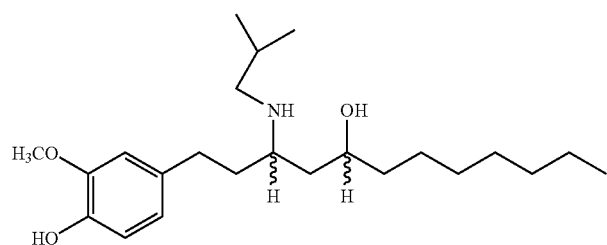 |
| 11 | 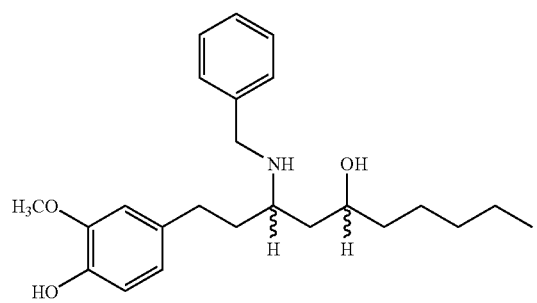 |
| 12 | 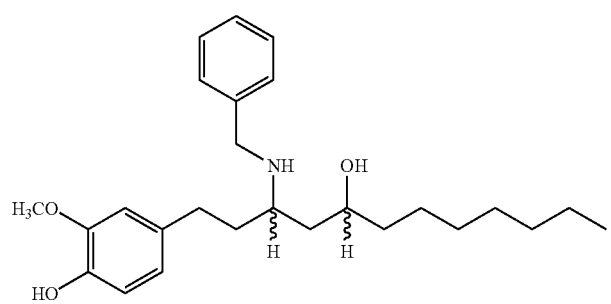 |
| 13 | 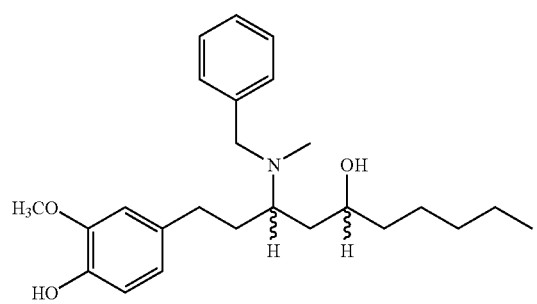 |

-continued

| Compound Number | Structure |
|---|---|
| 14 | [structure: 4-hydroxy-3-methoxyphenyl ethyl chain connected to CH(N(Bn)(Me))–CH(OH)–C7H15] |
| 15 | [structure: bornyl-pyrrolidine] |
| 16 | [structure: pyrrolidinyl-CH2-CH2-CH2-CH=C(CH3)2] |
| 17 | [structure: pyrrolidine-CH(–)-CH2-CH2-CH=C(CH3)2 branch] |
| 18 | [structure: pyrrolidine-CH2-CH(–)-CH2-CH2-CH=C(CH3)2] |

Figure 3:
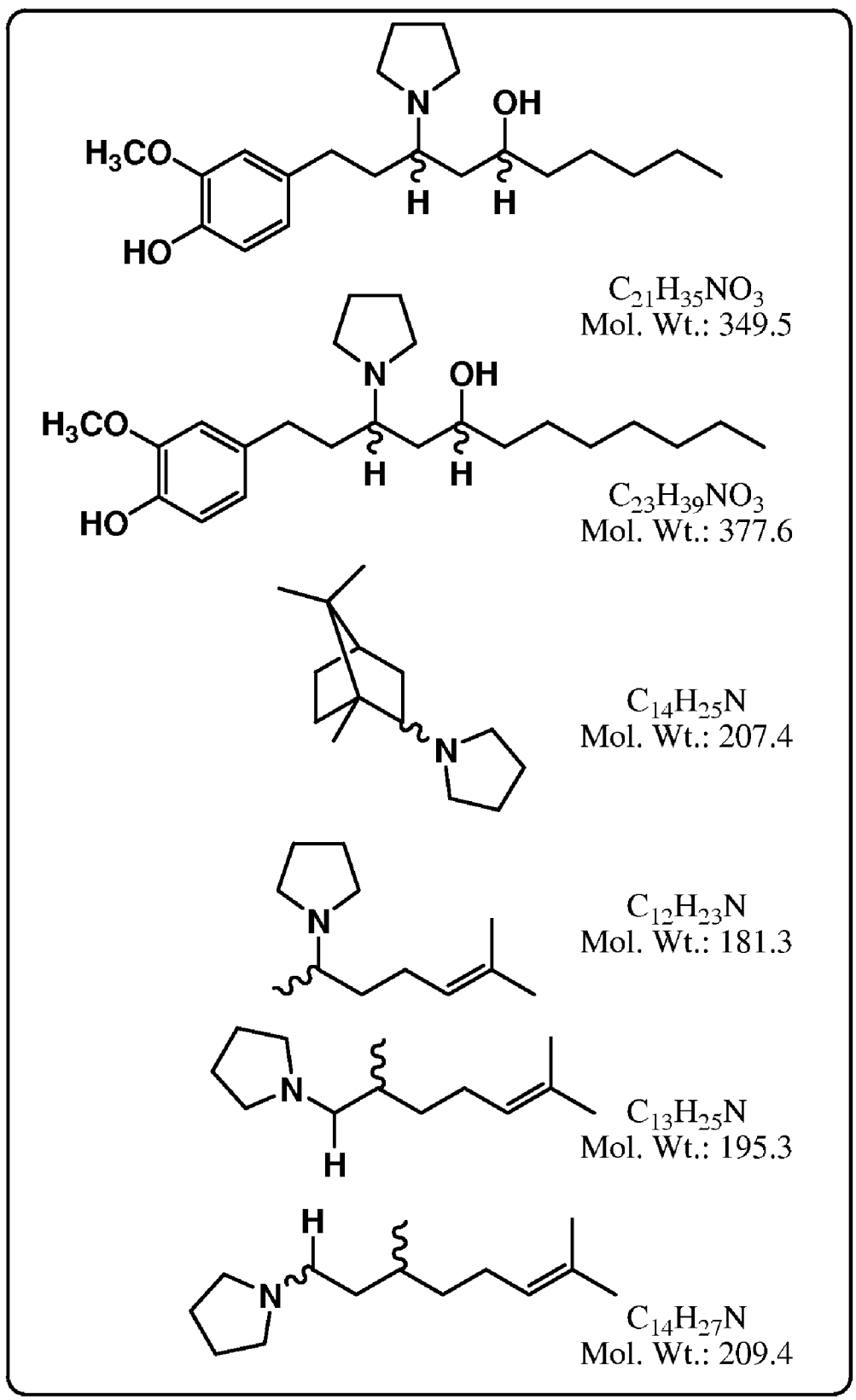
FIG. 3 shows isolated compounds of the invention having superior activity in a beta-secretase assay for the treatment of cognitive impairment and Alzheimer's disease.

Other preferred compounds according to the present invention are shown, for example, in FIG. 1, FIG. 2, and FIG. 3. FIG. 1 illustrates aromatic compounds of the invention for the treatment of cognitive impairment and Alzheimer's disease. FIG. 2 illustrates non-aromatic compounds of the invention for the treatment of cognitive impairment and Alzheimer's disease; and FIG. 3 shows isolated compounds of the invention having superior activity in a beta-secretase assay for the treatment of cognitive impairment and Alzheimer's disease.

According to another embodiment, a compound of any of the above Formulas I, II, and/or III, including compound numbers 1-18, and/or pharmaceutically acceptable salts and prodrugs thereof which exhibit activity in a beta-secretase assay are provided.

According to another embodiment, a compound of any of the above Formulas I, II, and/or III, including compound numbers 1-18, and/or pharmaceutically acceptable salts and prodrugs thereof formulated together with one or more pharmaceutically-acceptable carriers is provided. The pharmaceutical compositions may be specially formulated for oral administration in solid or liquid form, for parenteral injection, or for vaginal or rectal administration.

Solid dosage forms for oral administration include capsules, tablets, pills, powders, and granules. In such solid dosage forms, the active compound is mixed with at least one inert, pharmaceutically-acceptable excipient or carrier including sodium citrate or dicalcium phosphate, for example, and/or fillers or extenders including starches, lactose, sucrose, glucose, mannitol, and silicic acid, for example; and/or binders including carboxymethylcellulose, alginates, gelatin, polyvinylpyrrolidone, sucrose, and acacia, for example; and/or humectants such as glycerol; and/or disintegrating agents including agar-agar, calcium carbonate, potato starch, tapioca starch, alginic acid, certain silicates, and sodium carbonate, for example; and/or solution retarding agents such as paraffin; and/or absorption accelerators such as quaternary ammonium compounds; and/or wetting agents including cetyl alcohol and glycerol monostearate, for example; and/or absorbents such as kaolin and bentonite clay, for example; and/or lubricants such as talc, calcium stearate, magnesium stearate, solid polyethylene glycols, sodium lauryl sulfate, for example; and mixtures of the foregoing ingredients.

In the case of solid dosage forms, such as tablets, dragees, capsules, pills, and granules, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms may also be prepared with coatings and shells such as enteric coatings and other coatings known in the pharmaceutical art. Dosage forms may optionally contain opacifying agents and may also be of a composition that they release the active ingredient(s) only, or preferentially, in a certain part of the intestinal tract, optionally, in a delayed manner. The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers, and mixtures thereof, as will be understood by those of skill in the art by reference to this disclosure. In addition to inert diluents, the oral compositions can also include adjuvants such as wetting agents, emulsifying and suspending agents, sweetening, flavoring, and perfuming agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption an injectable pharmaceutical form may be brought about by the inclusion of agents which delay absorption such as aluminum monostearate and gelatin. In some cases, it is desirable to slow the absorption of the drug from subcutaneous or intramuscular injection. This may be accomplished by the use of a liquid suspension of crystalline or amorphous material with poor water solubility. Alternatively, delayed absorption of a parenterally administered drug form is accomplished by dissolving or suspending the drug in an oil vehicle.

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio, such as known to those of skill in the art. The salts may be prepared in situ during the final isolation and purification of the compounds of the invention or separately by reacting a free base with a suitable acid.

Actual dosage levels of active ingredients in the pharmaceutical compositions of this invention may be varied so as to obtain an amount of the active compound or compounds that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. If desired, the effective daily dose may be divided into multiple doses for purposes of administration, e.g. two to four separate doses per day.

According to another embodiment, the invention comprises a method of inhibiting, treating, or abatement of cognitive decline and/or Alzheimer's disease in a mammal, the method comprising administering a derivative of ginger oil to a mammal. Preferably, the derivative is a nitrogen-containing derivative, meaning that the derivative has one or more nitrogen containing groups such as an amino group. According to the method, the symptom of cognitive decline and/or Alzheimer's disease is one or more of memory loss, confusion, impaired judgment, personality changes, disorientation, and loss of language skills.

According to a preferred embodiment of the method, the inhibiting, treating, or abatement of cognitive decline and/or Alzheimer's disease comprises one or more of restoration of long term potentiation; and/or inhibiting, treating, or abatement of one or both of neurodegeneration and general amyloidosis. Also according to a preferred embodiment of the method, inhibiting, treating, or abatement of cognitive decline comprises inhibiting, treating, or abatement of one or more of amyloid production, amyloid assembly, amyloid aggregation, amyloid oligomer binding, and amyloid deposition.

According to another preferred embodiment of the method, the derivative of ginger oil is a compound in purified and isolated form, and more preferably, the derivative of ginger oil is a nitrogen-containing compound in purified and isolated form.

According to another embodiment, a method of inhibiting, treating, or abatement of cognitive decline and/or Alzheimer's disease in a patient by administering a compound according to the invention to the patient is provided. Preferably, the compound is a compound of any of the above Formulas I, II, and/or III, including compound numbers 1-18, and/or pharmaceutically acceptable salts or prodrugs thereof.

According to another embodiment, a method of preparing an array of chemical compounds from a biological extract is provided. Preferably, the method comprises preparing an array of nitrogen-containing chemical compounds from a biological extract.

The method of the invention, termed "chemical conditioning" is generally applicable to all biological extracts, in particular, natural plant extracts, common or medicinal. Chemical conditioning is a method which produces novel unnatural drug-like compounds from readily available natural materials. In general, the "chemical conditioning" of natural extracts coupled with pre-fractionation of the chemically conditioned extracts facilitates successful biochemical screening of extracts by destroying reactive natural compounds that generate false positive results in biochemical assays. Chemical conditioning produces novel lead-like and drug-like compounds and, the reductive amination protocol described here can produce structurally diverse nitrogen-containing products that are particularly lead-like and drug-like.

The method of the present invention is exemplified in Scheme I below. According to the method, first, a biological extract, e.g., a plant extract is provided, the biological extract has one or more biological compounds, each biological compound having one or more reactive electrophilic groups. Next, the biological compounds in the biological extract are reacted with an amine to incorporate the amine into the biological compounds. Next, the biological compounds having the incorporated amine are reacted with a reducing agent to reduce the intermediate imine and enamine compounds and form one or more nitrogen-containing chemical compounds. Thus, the resultant nitrogen-containing chemical compounds are derivatives of the biological compounds in the biological extract. Preferably, the biological compounds in the biological extract are compounds having ketones and aldehydes that are reacted with various amines. This reaction is followed by hydride reduction of the intermediate imines and enamines to provide secondary and tertiary amines. The reaction of ketones and aldehydes with amines, followed by reduction to form imines and enamines is known in the art.

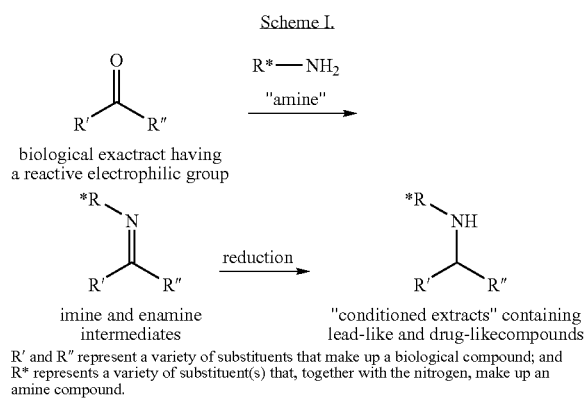

Scheme I.

biological exactract having a reactive electrophilic group imine and enamine intermediates "conditioned extracts" containing lead-like and drug-likecompounds R' and R" represent a variety of substituents that make up a biological compound; and R* represents a variety of substituent(s) that, together with the nitrogen, make up an amine compound.

The chemical conditioning method described herein employs a biological extract, using many different reagents, to efficiently produce an array of nitrogen-containing chemical compounds. The ready commercial availability of many low molecular weight amines for use as inputs in the reductive amination sequence enables the development of many different and structurally diverse central nervous system druglike mixtures from the same natural extract. Suitable amines for use in the present method are selected from the group consisting of primary amines, secondary amines, cyclic amines, pyrollidine, and amino acids. Suitable reducing agents for use in the present method are selected from the group of hydride reducing agents including but not limited to sodium borohydride, sodium triacetoxyborohydride, and lithium aluminum hydride.

The method may further comprise quenching the reaction a quenching agent, wherein the quenching agent is selected from but not limited to the group consisting of sodium bicarbonate, sodium carbonate, sodium sulfate, sodium sulfate decahydrate. The method may also further comprise isolating one or more of the nitrogen-containing chemical compounds, in a purified or unpurified form. The resultant nitrogen-containing chemical may then be screened or tested for biological activity.

The process of chemical conditioning by reductive amination described herein destroys reactive electrophiles in the natural extract, including ketones, as in the gingerols, and converts them to chemically stable compounds such as amines. The resulting conditioned extracts contain both natural compounds and novel unnatural nitrogen-containing amine products that are potential drug candidates. In the case of the extracts of gingerol, the nitrogen-containing amine products are potential central nervous system drugs.

In a preferred embodiment of the invention, a plant extract is obtained from ginger root. Natural ginger oil contains hundreds of small molecules including the well-characterized aromatic gingerol series of ketones shown in Table I below.

TABLE I

| Compound Structure | Common Name |
|---|---|
| 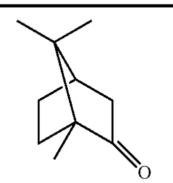 | Camphor |
| 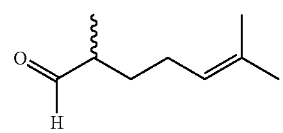 | Bergamal |
| 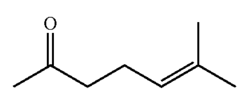 | Prenylacetone |
| 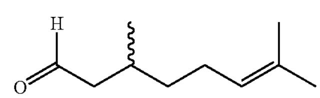 | Citronelal |

A representation of known volatile, non-aromatic components of ginger oil that have been previously characterized is shown in Table II below.

TABLE II

| Compound Structure | Alkyl Chain Length (n) Substituent (R) | Common Name |
|---|---|---|
|  | n = 4 | [6]-gingerol |
|  | n = 6 | [8]-gingerol |
|  | n = 8 | [10]-gingerol |

TABLE II-continued

| Compound Structure | Alkyl Chain Length (n) Substituent (R) | Common Name |
|---|---|---|
| (shogaol structure: H3CO/HO-phenyl-CH2CH2-C(=O)-CH=CH-(CH2)nCH3) | n = 2<br>n = 4<br>n = 5<br>n = 6<br>n = 8<br>n = 10 | [5]-shogaol<br>[6]-shogaol<br>[7]-shogaol<br>[8]-shogaol<br>[10]-shogaol<br>[12]-shogaol |
| (gingerdiol structure: H3CO/HO-phenyl-CH2CH2-CH(OH)-CH2-CH(OH)-(CH2)nCH3) | n = 4<br>n = 6<br>n = 8 | [6]-gingerdiol<br>[8]-gingerdiol<br>[10]-gingerdiol |
| (dehydrogingerdione structure: H3CO/HO-phenyl-CH=CH-C(=O)-CH2-C(=O)-(CH2)nCH3) | n = 4<br>n = 6<br>n = 8 | [6]-dehydrogingerdione<br>[8]-dehydrogingerdione<br>[10]-dehydrogingerdione |
| (gingerdione structure: H3CO/HO-phenyl-CH2CH2-C(=O)-CH2-C(=O)-(CH2)nCH3) | n = 4<br>n = 6<br>n = 8 | [6]-gingerdione<br>[8]-gingerdione<br>[10]-gingerdione |
| (paradol structure: H3CO/HO-phenyl-CH2CH2-C(=O)-CH2CH2-(CH2)nCH3) | n = 4 | [6]-paradol |
| (gingerdiol acetate structure: H3CO/HO-phenyl-CH2CH2-CH(OAc)-CH2-CH(OR)-(CH2)nCH3) | n = 4; R = H<br>n = 4; R = AC | [6]-gingerdiol-3-monoacetate<br>[6]-gingerdiol-3,5-diacetate |
| (furan structure: H3CO/HO-phenyl-CH2CH2-furan-(CH2)nCH2CH3) | n = 2<br>n = 4<br>n = 6 | |

A specific example of the chemical conditioning process of the invention is shown in Scheme II below. Scheme II shows the two-step reductive amination chemical conditioning protocol performed on ginger oil and ginger oleoresin in accordance with a preferred embodiment of the method, wherein gingerol analogues having a β-hydroxycarbonyl function are converted to amino alcohols. According to the method shown in Scheme II, first, an extract of ginger containing one or more gingerols (A) and other small molecules occurring in natural ginger extract is reacted with an amine, (B). Then, the resultant compound (C) is then reduced, with a reducing agent (D) to from the nitrogen-containing compounds (E).

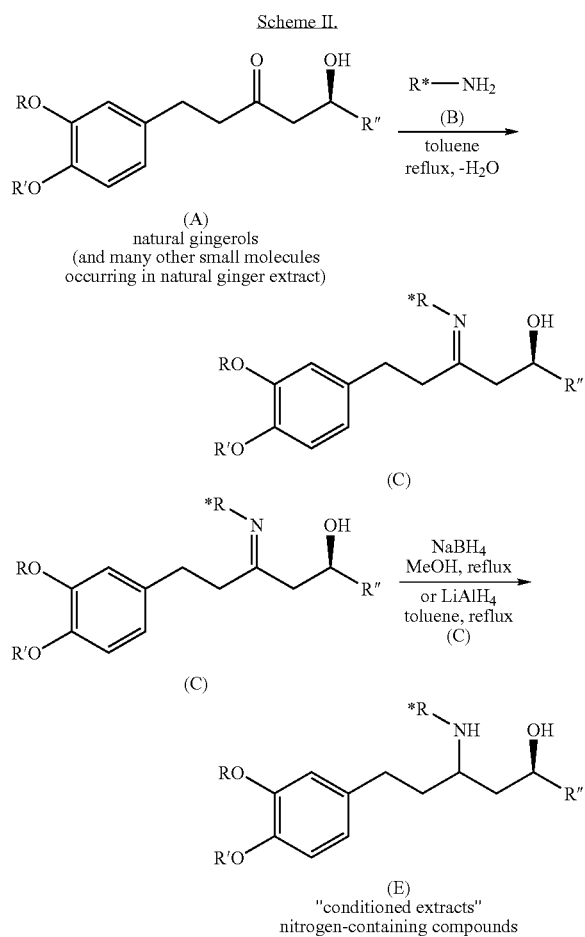

Scheme II.

(A) natural gingerols (and many other small molecules occurring in natural ginger extract)

(C)

(C)

(E) "conditioned extracts" nitrogen-containing compounds

In the next step of the method, one, or more than one derivative is isolated from the extract. The conditioned extracts are typically fractionated by flash chromatography and the fractions are tested for enzyme inhibitor activity and receptor binding affinity in Alzheimer's disease-relevant assays. Further isolation and characterization of biologically active compounds may follow.

New lead compounds generated by this chemical conditioning method may then be prepared on preparative scale via multi-kilogram SFE followed by the same chemical conditioning protocol described herein.

In another embodiment, the present invention comprises an isolated derivatives made in accordance with the foregoing reductive amination process having the properties of a central nervous system drug candidate. Desirable properties include potential oral bioavailability, potential membrane permeability and/or a low molecular weight. Preferably the molecular weight of the derivative is less than about 550 Daltons, more preferably from about 250 to about 450 Daltons. Most preferably, the derivatives of ginger oil possesses beta-secretase inhibitory activity, and/or inhibit amyloid production, amyloid assembly, amyloid aggregation, amyloid oligomer binding, or amyloid deposition.

Preliminary data has demonstrated proof-of-principle in that beta-secretase inhibitory activity has been observed in our conditioned extracts where there was no inhibitory activity in natural ginger oil. The isolation and characterization of beta-secretase inhibitors as new lead compounds for the treatment of cognitive decline and Alzheimer's disease has produced a new structure-activity-relationship and has yielded the promising beta-secretase inhibitors shown, for example in FIGS. 1-3. These compounds are potential therapeutic agents for the treatment and prevention of cognitive decline, amyloid production, neurodegeneration, and Alzheimer's disease.

The invention may be appreciated in certain aspects with reference to the following examples, offered by way of illustration, not by way of limitation. Materials, reagents and the like to which reference is made in the following examples are obtainable from commercial sources, unless otherwise noted.

EXAMPLES

Materials And Methods
  Ginger Oil
  The light oil extract from ginger root was obtained by supercritical $CO_2$ extraction.
  Ginger Oleoresin
  The heavy remainder oil was obtained following extraction of ginger root by supercritical $CO_2$ extraction.

Conditioned Extraction of Ginger Oil
  Reductive Amination of Ginger Oil (Method 1):
  Ginger oil (10 g) was dissolved in toluene (250 mL) and pyrrolidine (4.5 mL) was added. The mixture was maintained under an atmosphere of nitrogen and heated at reflux with removal of water by Dean-Stark distillation for 16 hr. At this time the Dean-Stark trap was removed and the reaction mixture was cooled to 0° C. on an ice bath. A solution of sodium borohydride (5 g) in methanol (50 mL) was added portion-wise over 30 minutes with vigorous stirring. When the addition was complete the mixture was heated to reflux for 16 hr. At this time the reaction mixture was cooled to room temperature and poured into saturated aqueous sodium bicarbonate (300 mL). The resulting mixture was concentrated by rotary evaporation and the aqueous residue was partitioned between water and chloroform. The chloroform layer was dried over anhydrous sodium sulfate and then filtered and concentrated. The product was then fractionated using silica gel column chromatography employing a gradient from 100% chloroform to chloroform:methanol (4:1). Six combined fractions from relatively non-polar to polar were collected and concentrated. Each fraction was submitted for biological testing. Beta-secretase enzyme assays were performed by MDS Pharma, Bothell, Washington, according to Fukumoto et al. (2004).

Reductive Amination of Ginger Oil (Method 2):
  Ginger oil (10 g) was dissolved in toluene (250 mL) and pyrrolidine (4.5 mL) was added. The mixture was maintained under an atmosphere of nitrogen and heated at reflux with removal of water by Dean-Stark distillation for 16 hr. At this time the Dean-Stark trap was removed and the reaction mixture was cooled to 0° C. on an ice bath. A solution of lithium aluminum hydride (58 mL, a 1 M solution in tetrahydrofuran) was added portion-wise by syringe over 30 minutes with vigorous stirring. When the addition was complete the mixture was heated to reflux for 16 hr. At this time the reaction mixture was cooled to 0° C. and the excess lithium aluminum hydride was quenched by portion-wise addition of sodium sulfate decahydrate. The resulting suspension was vacuum filtered through a bed of sand and Celite. The collected solids were rinsed with tetrahydrofuran (3×100 mL) and then once with a solution of chloroform:methanol (4:1). The filtrate was concentrated by rotary evaporation and the residue was partitioned between water and chloroform. The chloroform layer was dried over anhydrous sodium sulfate and then filtered and concentrated. The product was then fractionated using silica gel column chromatography employing a gradient from 100% chloroform to chloroform:methanol (4:1). Six combined fractions from relatively non-polar to polar were collected and concentrated. Each fraction was submitted for biological testing. Beta-secretase enzyme assays were performed by MDS Pharma, Bothell, Washington, according to Fukumoto et al. (2004).

Conditioned Extraction of Ginger Oleoresin:
  Reductive Amination of Ginger Oleoresin (Method 1):
  Ginger oleoresin (10 g) was dissolved in toluene (250 mL) and pyrrolidine (4.5 mL) was added. The mixture was maintained under an atmosphere of nitrogen and heated at reflux with removal of water by Dean-Stark distillation for 16 hr. At this time the Dean-Stark trap was removed and the reaction mixture was cooled to 0° C. on an ice bath. A solution of sodium borohydride (5 g) in methanol (50 mL) was added portion-wise over 30 minutes with vigorous stirring. When the addition was complete the mixture was heated to reflux for 16 hr. At this time the reaction mixture was cooled to room temperature and poured into saturated aqueous sodium bicarbonate (300 mL). The resulting mixture was concentrated by rotary evaporation and the aqueous residue was partitioned between water and chloroform. The chloroform layer was dried over anhydrous sodium sulfate and then filtered and concentrated. The product was then fractionated using silica gel column chromatography employing a gradient from 100% chloroform to chloroform:methanol (4:1). Six combined fractions from relatively non-polar to polar were collected and concentrated. Each fraction was submitted for biological testing. Beta-secretase enzyme assays were performed by MDS Pharma, Bothell, Washington, according to Fukumoto et al. (2004).

Reductive Amination of Ginger Oleoresin (Method 2):
  Ginger oleoresin (10 g) was dissolved in toluene (250 mL) and pyrrolidine (4.5 mL) was added. The mixture was maintained under an atmosphere of nitrogen and heated at reflux with removal of water by Dean-Stark distillation for 16 hr. At this time the Dean-Stark trap was removed and the reaction mixture was cooled to 0° C. on an ice bath. A solution of lithium aluminum hydride (58 mL, a 1 M solution in tetrahydrofuran) was added portion-wise by syringe over 30 minutes with vigorous stirring. When the addition was complete the mixture was heated to reflux for 16 hr. At this time the reaction mixture was cooled to 0° C. and the excess lithium aluminum hydride was quenched by portion-wise addition of sodium sulfate decahydrate. The resulting suspension was vacuum filtered through a bed of sand and Celite. The collected solids were rinsed with tetrahydrofuran (3×100 mL) and then once with a solution of chloroform:methanol (4:1). The filtrate was concentrated by rotary evaporation and the residue was partitioned between water and chloroform. The chloroform layer was dried over anhydrous sodium sulfate and then filtered and concentrated. The product was then fractionated using silica gel column chromatography employing a gradient from 100% chloroform to chloroform:methanol (4:1). Each fraction was submitted for biological testing. Beta-secretase enzyme assays were performed by MDS Pharma, Bothell, Washington, according to Fukumoto et al. (2004).

General Observations:
  The biologically active fractions were generally found to be the relatively polar fractions. These fractions had been newly generated by the chemical conditioning process, in this particular case, by reductive amination. The relatively polar active fraction was not present in the natural ginger oil or in the natural ginger oleoresin as analyzed by chromatography. Several conditioned extractions of ginger oil and ginger oleoresin were performed using a variety of amines to generate a structure-activity-relationship between analogous compounds derived by reductive amination (Table III). The examples shown are derived from the gingerol series of compounds occurring in the natural starting materials. The preferred beta-secretase inhibitors are shown in FIG. 6.

TABLE III

Structure-activity-relationship of aromatic inhibitors.

| Example | Structure | MW | Beta-secretase activity |
| --- | --- | --- | --- |
| 1 | 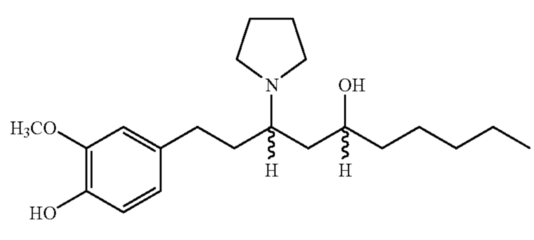 | 349.5 | +++ |
| 2 | 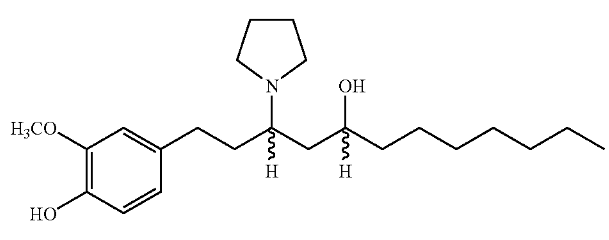 | 377.5 | +++ |

TABLE III-continued

Structure-activity-relationship of aromatic inhibitors.

| Example | Structure | MW | Beta-secretase activity |
|---------|-----------|------|------|
| 3 | 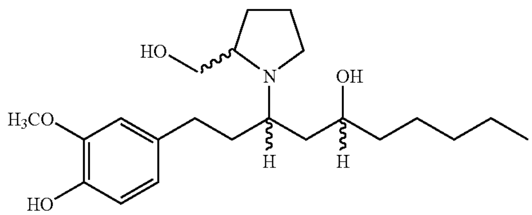 | 379.5 | ++ |
| 4 | 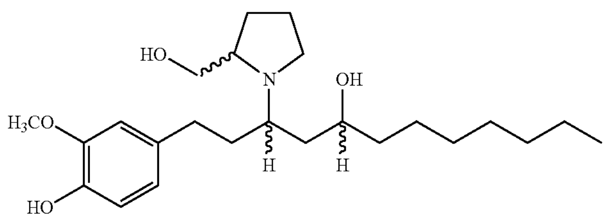 | 407.6 | ++ |
| 5 | 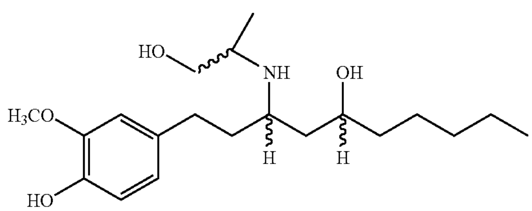 | 353.5 | + |
| 6 | 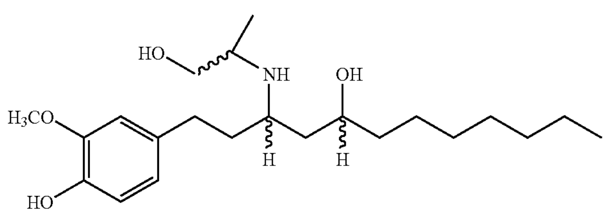 | 381.5 | + |
| 7 | 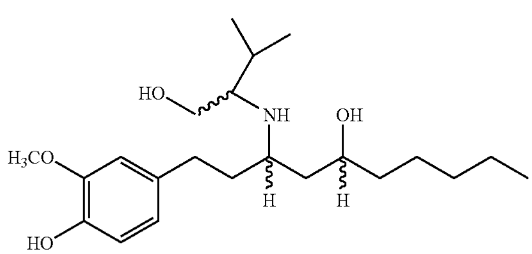 | 381.5 | + |
| 8 | 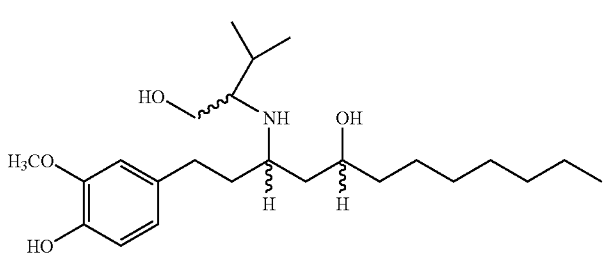 | 409.6 | + |

TABLE III-continued

Structure-activity-relationship of aromatic inhibitors.

| Example | Structure | MW | Beta-secretase activity |
|---------|-----------|------|-------------------------|
| 9 | 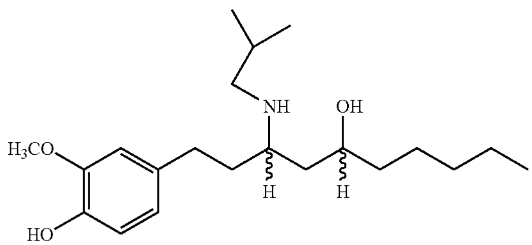 | 351.5 | ++ |
| 10 | 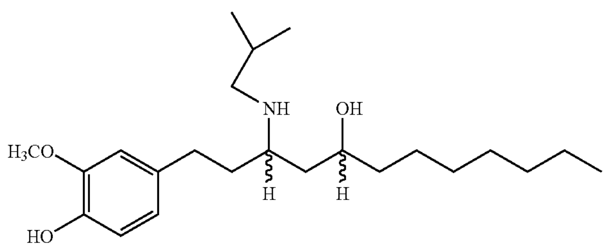 | 379.6 | ++ |
| 11 | 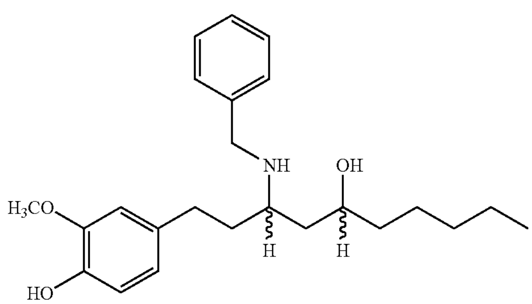 | 385.5 | + |
| 12 | 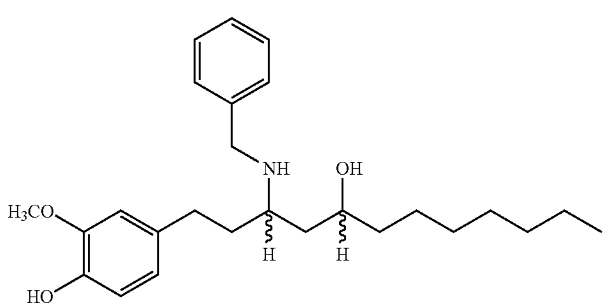 | 413.6 | + |
| 13 | 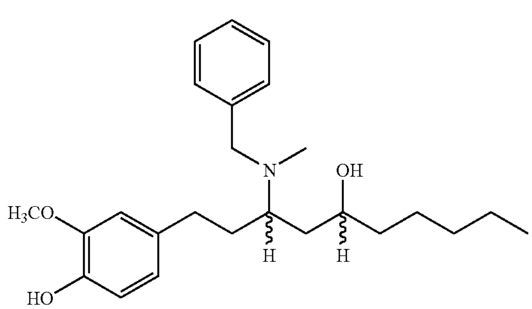 | 399.6 | ++ |

TABLE III-continued

Structure-activity-relationship of aromatic inhibitors.

| Example | Structure | MW | Beta-secretase activity |
|---|---|---|---|
| 14 | 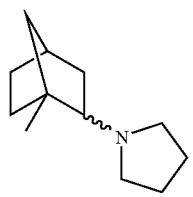 | 427.6 | ++ |

TABLE 2

Structure-activity-relationship of non-aromatic inhibitors.

| Example | Structure | MW | Beta-secretase activity |
|---|---|---|---|
| 15 | 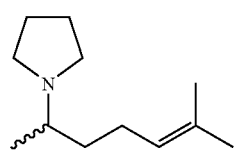 | 207.4 | +++ |
| 16 | 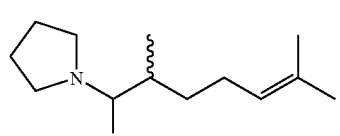 | 181.3 | +++ |
| 17 | 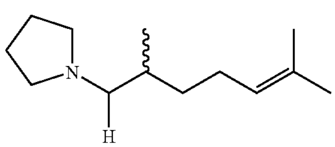 | 195.3 | ++ |
| 18 | 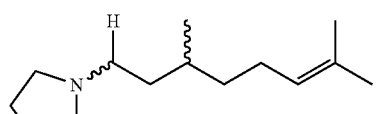 | 209.4 | ++ |

Conclusion

As described herein, compounds derived from ginger oil that show activity in a beta-secretase inhibitor assay have been developed. Methods for the treatment, inhibition, and abatement of cognitive decline and Alzheimer's disease employing the compounds of the present invention are also described herein. The compounds of the present invention have been created and discovered using a two-step reductive amination chemical conditioning procedure. This two-step reductive amination chemical conditioning procedure, also described herein, was performed on ginger root extract to arrive at the compounds of the invention. However, this method should be generally applicable to other biological, i.e., natural extracts to generate novel drug-like compounds for screening for biological activity, and new drug discovery.

Although the present invention has been described in considerable detail with reference to certain preferred versions thereof, other versions are possible. Therefore, the spirit and scope of the invention should not be limited to the description of the preferred versions described herein.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features.

All references cited in this disclosure are incorporated herein by reference in their entirety.

What is claimed:

1. A compound of the formula:

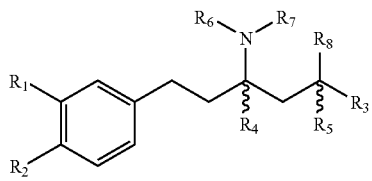

or a pharmaceutically acceptable salt thereof, wherein, $R_1$, and $R_2$ are each independently selected from the group consisting of hydrogen, hydroxy, methoxy, halide, haloalkyl, small alkyl, and small alkoxy;

$R_3$, $R_4$ and $R_5$ are each independently selected from the group consisting of hydrogen, small alkyl, cycloalkyl, heterocyclyl, heterocyclylalkyl, aryl, arylalkyl, heteroaryl, and heteroarylalkyl;

$R_6$ and $R_7$ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or $R_6$ and $R_7$ along with the nitrogen to which they are attached form a five or six membered heterocyclic ling, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —$CH_2OR_9$;

$R_8$ is selected from the group consisting of hydroxy, small alkoxy, and —$NR_{10}R_{11}$;

$R_9$ is selected from the group consisting of hydrogen, small alkyl, cycloalkyl, heterocyclyl, heterocyclylalkyl, aryl, arylalkyl, heteroaryl, and heteroarylalkyl; and $R_{10}$ and $R_{11}$ are each independently selected from the group consisting of hydrogen, small alkyl, hydroxyalkyl, cycloalkyl, heterocyclyl, heterocyclylalkyl, aryl, arylalkyl, heteroaryl, and heteroarylalkyl; or $R_{10}$ and $R_{11}$ along with the nitrogen to which they are attached form a five or six membered heterocyclic ring, comprising one or two heteroatoms selected from the group consisting of oxygen, sulfur and nitrogen, wherein the five or six membered heterocyclic ring is unsubstituted, or substituted with a substituent selected from the group consisting of hydroxy, hydroxyalkyl, halide, haloalkyl, small alkyl, small alkoxy, and —$CH_2OR_9$.

2. A compound according to claim 1 of the formula:

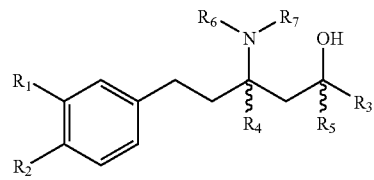

or a pharmaceutically acceptable salt thereof, wherein, $R_6$ and $R_7$ along with the nitrogen to which they are attached form a five or six membered heterocyclic ring of the formula:

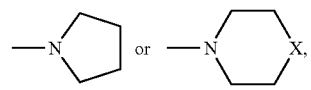

wherein,

X is selected from the group consisting of —$CH_2$, —$CHR_{17}$, —N=, —O—, —S—, and —$NR_{17}$, wherein each carbon atom of the five or six membered heterocyclic ring, individually, is unsubstituted, or substituted with a substituent selected from the group consisting of hydroxy, hydroxyalkyl, halide, haloalkyl, small alkyl, small alkoxy, and $CH_2OR_9$; and $R_{17}$ is selected from the group consisting of hydrogen, small alkyl, hydroxyalkyl, cycloalkyl, heterocyclyl, heterocyclylalkyl, aryl, arylalkyl, heteroaryl, and heteroarylalkyl.

3. A compound according to claim 1 of the formula:

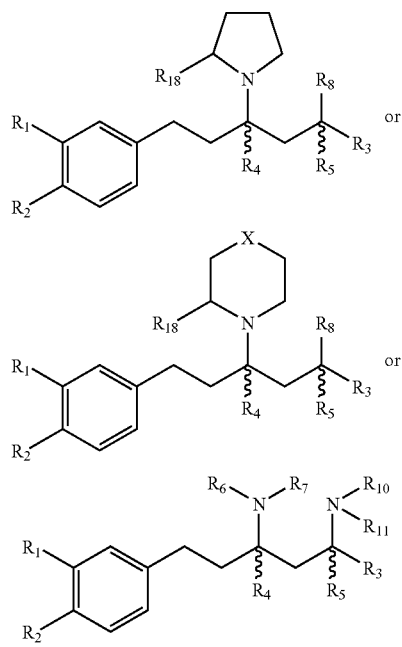

or a pharmaceutically acceptable salt thereof, wherein, $R_{18}$ is selected from the group consisting of hydrogen, hydroxy, hydroxyalkyl, halide, haloalkyl, small alkyl, small alkoxy, and —$CH_2OR_9$.

4. A compound according to claim 3 of the formula:

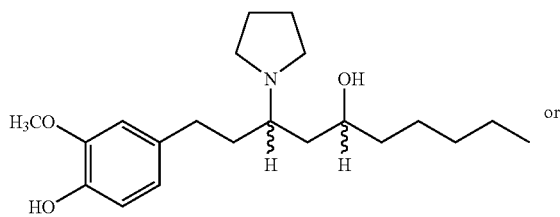 or

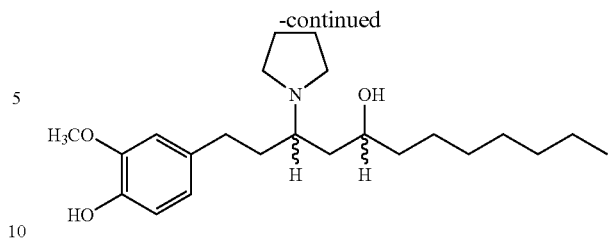

or a pharmaceutically acceptable salt thereof.

5. A compound according to claim 1 wherein the compound exhibits activity in a betasecretase assay, or a pharmaceutically acceptable salt thereof.

6. A composition comprising a compound according to claim 1 or a pharmaceutically acceptable salt thereof and a pharmaceutically-acceptable carrier.

* * * * *